United States Patent [19]
Makino et al.

[11] Patent Number: 5,852,109
[45] Date of Patent: Dec. 22, 1998

[54] POLY-α-AMINO ACID PARTICLES, EMULSIONS CONTAINING THE SAME AND PROCESS FOR PREPARING THE SAME

[75] Inventors: Kenya Makino, Tsuchiura; Seiji Fukuhara, Kawagoe; Kyoko Kuroda, Tsuchiura; Toshio Hayashi, Kyoto, all of Japan

[73] Assignee: JSR Corporation, Tokyo, Japan

[21] Appl. No.: 526,694

[22] Filed: Sep. 11, 1995

[30] Foreign Application Priority Data

Sep. 9, 1994 [JP] Japan .................................. 6-240751
Oct. 28, 1994 [JP] Japan .................................. 6-287198

[51] Int. Cl.[6] .................................................. C08L 37/00
[52] U.S. Cl. ........................ 524/811; 524/602; 524/606; 524/608; 524/808; 524/827; 524/850; 524/879; 424/489; 424/497; 526/258; 526/260; 528/271; 528/292; 528/328
[58] Field of Search ..................... 524/808, 811, 524/827, 602, 606, 608, 850, 879; 526/260, 258; 424/489, 497; 528/271, 292, 328

[56] References Cited

U.S. PATENT DOCUMENTS 3,658,831  4/1972  Fujimoyo et al. ..................... 548/227
4,525,495  6/1985  Dorman et al. ........................ 524/606
4,694,044  9/1987  Kiniwa ................................... 524/606
4,840,975  6/1989  Hirayama et al. ..................... 521/183
4,999,386  3/1991  Oakes et al. ....................... 526/260 X

*Primary Examiner*—Jody M. Reddick
*Attorney, Agent, or Firm*—Oblon, Spivak, McClelland, Maier & Neustadt, P.C.

[57] ABSTRACT

Solid poly-α-amino acid particles are obtained by preparing an oil-in-water emulsion from water and an organic solvent having a water solubility of 10 g/100 ml or less, and polymerizing an α-amino acid-N-carboxy anhydride by emulsion polymerization in the oil-in-water emulsion, or by polymerizing an α-amino acid-N-carboxy anhydride in water in the presence of an emulsifier and an initiator. Hollow particles can be obtained by adding a poor solvent for the poly-α-amino acid to the poly-α-amino acid particles and removing the solvents. These poly-α-amino acid particles are useful as a novel raw materials for coating on papers, rubbers and fibers, for encapsulating cosmetics, drugs, agricultural chemicals and fertilizers, and as particles for diagnostic reagents.

15 Claims, No Drawings

POLY-α-AMINO ACID PARTICLES, EMULSIONS CONTAINING THE SAME AND PROCESS FOR PREPARING THE SAME

BACKGROUND OF THE INVENTION

1. Field of the Invention

The present invention relates to novel poly-α-amino acid particles which are useful as raw materials for coating on papers, resins, rubbers and fibers, for encapsulating cosmetics, drugs, agricultural chemicals and fertilizers, and as particles for diagnostic reagents. The present invention also relates to emulsions containing such poly-α-amino acid particles and processes for preparing such poly-α-amino acid particles by emulsion polymerization of an α-amino acid-N-carboxy anhydride (α-amino acid-NCA) in an aqueous medium.

2. Discussion of the Background

Polymer particle emulsions known in the art, in which polymer particles are dispersed in an aqueous medium, include those of styrene-butadiene copolymers, styrene-butadiene-acrylonitrile copolymer, and the like. These emulsions are directly manufactured by emulsion polymerization and used in various applications such as adhesives and coating materials for papers.

Poly-α-amino acids are polymers which exhibit excellent characteristics for protecting the natural environment, due to their various beneficial characteristics; they are decomposed by microorganisms, allow oxygen and water to permeate therethrough, and possess a high wear resistance.

If hollow particles of poly-α-amino acid could be obtained, such particles would be useful in drug delivery applications by encapsulating drugs therein, by utilizing the in vivo degradation characteristics of the poly-α-amino acid. If agricultural chemicals or fertilizers were encapsulated or carried therein, such poly-α-amino acid particles would be useful as sustained-release agricultural chemicals or fertilizers, wherein the poly-α-amino acid is decomposed gradually in the earth. Furthermore, if cosmetics were encapsulated or retained therein, these poly-α-amino acid particles would be useful as cosmetics wherein the water-retention characteristic of poly-α-amino acid is utilized.

Conventional methods for manufacturing poly-α-amino acids include a method of polymerizing an α-amino acid NCA (hereinafter referred to as amino acid-NCA), dissolved in an organic solvent which does not contain water by homogeneous solution polymerization; and a method of polymerizing an amino acid-NCA at the interface of a hydrophobic organic solvent layer in which the amino acid-NCA is dissolved and a water layer in which a polymerization initiator is dissolved (Japanese Patent Application Laid-open (kokai) No. 57096/1974).

On the other hand, only one method is currently known for preparing an emulsion in which poly-α-amino acid particles are dispersed in an aqueous medium. This is a method comprising preparing a poly-α-amino acid solution by the conventional homogeneous solution polymerization of amino acid-NCA in an organic solvent, emulsifying this solution by the addition of water and an emulsifier thereto, and removing the organic solvent. No other effective method is known. This is because amino acid-NCA monomers are very easily hydrolyzed and rapidly decomposed in water or in the presence of a large amount of a compound containing exchangeable protons. This prevents a high degree of the polymerization reaction of the amino acid-NCA. It is thus difficult to produce poly-α-amino acid particles having a sufficiently high molecular weight.

Even in this conventional method, it is very difficult to disperse poly-α-amino acid particles with the desired small particle size in the emulsion. The average particle size in the resulting emulsion is comparatively large. It is impossible to obtain an emulsion of poly-α-amino acid particles having a small average particle size, for example, of 1 μm or less. In addition, the particle size distribution in the resulting emulsions is broad. It is difficult to obtain emulsions of poly-α-amino acids with a uniform particle size.

Furthermore, hollow particles of poly-α-amino acids have not previously been known.

Thus, there remains a need for emulsions of poly-α-amino acid particles having a small average particle size distribution. There also remains a need for emulsions of poly-α-amino acid particles having a narrow particle size distribution. There further remains a need for hollow poly-α-amino acid particles. In addition, there remains a need for processes for preparing such emulsions and particles.

SUMMARY OF THE INVENTION

Accordingly, it is one object of the present invention to provide novel emulsions of poly-α-amino acid particles.

It is another object of the present invention to prepare emulsions of poly-α-amino acid particles having a small average particle size.

It is another object of the present invention to prepare emulsions of poly-α-amino acid particles having a narrow particle size distribution.

It is another object of the present invention to provide processes for preparing such emulsions.

It is another object of the present invention to provide novel poly-α-amino acid particles.

It is another object of the present invention to provide novel hollow poly-α-amino acid particles.

It is another object of the present invention to provide a process for preparing such poly-α-amino acid particles.

These and other objects, which will become apparent during the following detailed description, have been achieved by the inventors' discovery that:

preparing an oil-in-water emulsion from water, an organic solvent having a water solubility of 10 g/100 ml or less under 1 atm at 25° C., and an emulsifier;

polymerizing an α-amino acid-NCA by emulsion polymerization in the oil-in-water emulsion; and removing said organic solvent, affords emulsions of poly-α-amino acid particles having a small average particle size and a narrow particle size distribution.

In a preferred embodiment of the present invention, the oil-in-water emulsion contains the α-amino acid-NCA in an oil phase.

In another preferred embodiment of the present invention, the α-amino acid-NCA is solid, this solid α-amino acid-NCA is added to the oil-in-water emulsion, and polymerized.

The inventors have also found that emulsions of poly-α-amino acid particles having a small average particle size and a narrow particle size distribution can be prepared by:

polymerizing an α-amino acid-NCA in an aqueous medium containing an emulsifier and a polymerization initiator.

The inventors have also found that the above object of preparing hollow particles of poly-α-amino acid has been achieved by the present invention by a process which comprises:

preparing an oil-in-water emulsion from water, an organic solvent having a water solubility of 10 g/100 ml or less under 1 atm. at 25° C., and an emulsifier;

polymerizing an α-amino acid-NCA by emulsion polymerization in the oil-in-water emulsion;

adding a solvent in which the poly-α-amino acid is only slightly soluble; and removing the solvents.

Other objects, features and advantages of the invention will hereinafter become more readily apparent from the following description.

DETAILED DESCRIPTION OF THE PREFERRED EMBODIMENTS

The process for the manufacture of poly-α-amino acid particles of the present invention is characterized by polymerizing an amino acid-NCA by emulsion polymerization in the presence of an emulsifier.

Specifically, it is desirable to use either of the following two methods: (1) production of an oil-in-water emulsion in which droplets, consisting of an amino acid-NCA and an organic solvent having a water solubility of 10 g/100 ml or less (hereinafter referred to as specific organic solvent), are dispersed in water, followed by the polymerization reaction, or (2) addition of an amino acid-NCA to water which contains a polymerization initiator and an emulsifier, followed by the polymerization reaction.

The amino acid-NCA can be prepared by heating an α-amino acid in the presence of phosgene to effect a dehydrochloric acid reaction.

First, illustrating the above process (1), the amino acid-NCA used as the monomer may be any amino acid NCA derived from any α-amino acid. When the amino acid-NCA is prepared from an α-amino acid having a functional group, such as a carboxyl group, a hydroxyl group, a thiol group, an amino group, a quanidyl group, or the like, in a side chain, it is necessary to convert the α-amino acid to the amino acid-NCA after protecting such a functional group with a suitable protective group.

The following examples are given as the α-amino acid which can be used in the present invention: (a) neutral amino acids, such as glycine, alanine, valine, norvaline, leucine, iso-leucine, norleucine, phenylalanine, methionine, and proline; (b) acidic amino acid-ω-esters (here, the esters are methyl ester, ethyl ester, propyl ester, butyl ester, octyl ester, 2-ethylhexyl ester, cyclohexyl ester, phenyl ester, benzyl ester, and the like), such as glutamic acid-γ-ester and aspartic acid β-ester; (c) N-acyl basic amino acids, such as N-carbobenzyloxylysine, N-carbobenzyloxyornithine, and N-acetyllysine; and (d) hydroxy or thiol group-containing α-amino acid esters (here, the esters are methyl ester, ethyl ester, propyl ester, butyl ester, octyl ester, 7-ethylhexyl ester, cyclohexyl ester, phenyl ester, benzyl ester, and the like), such as serine, threonine, cysteine, and tyrosine.

Of these α-amino acids, glutamic acid-γ-ester, N-carbobenzyloxylysine, alanine, leucine, and the like are preferred. The structure of some preferred amino acid-NCAs are shown below:

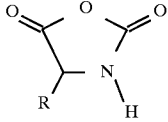

| R | amino acid-NCA |
|---|---|
| $-CH_3$ | alanine-NCA |
| $-CH_2CH_2CH_2CH_3$ | leucine-NCA |
| $-CH_2CH_2CO_2CH_3$ | glutamic acid-NCA methyl ester |
| $-(CH_2)_4-NCO_2CH_2Ph$ | N-ε-carbobenzyloxylysine-NCA |

The amino acid-NCA which can be obtained from these α-amino acids may be an optically active isomer, a racemate, or a mixture of these. It is possible to use two or more kinds of amino acid-NCAs together.

Particularly preferred amino acid-NCAs are γ-benzyl-L-glutamate-NCA, γ-methyl-L-glutamate-NCA, γ-ethyl-L-glutamate-NCA, N-carbobenzyloxylysine-NCA, and the like.

The specific organic solvent used in the present invention is an organic solvent which has a water-solubility of 10 g/100 ml or less, preferably 5 g/100 ml or less, under 1 atm at 25° C.

It is desirable that the specific organic solvent be capable of dissolving the amino acid-NCA in an amount of at least 0.1 g/100 ml, preferably at least 0.3 g/100 ml. Furthermore, it is desirable that the specific organic solvent, dissolve the poly-α-amino acid in an amount of at least 0.3 g/100 ml, preferably at least 0.5 g/100 ml.

If a specific organic solvent having a water solubility of greater than 10 g/100 ml is used, the water dissolved in the specific organic solvent in the step of preparing the base emulsion hydrolyzes the amino acid-NCA, causes a decrease in the polymerization yield, and makes it difficult to produce a high molecular weight poly-α-amino acid.

The following solvents are given as examples of the specific organic solvent: (a) halogenated aliphatic hydrocarbons, such as chloromethane, dichloromethane, chloroform, 1,1-dichloroethane, 1,2-dichloroethane, and 1,1,2-trichloroethane; (b) halogenated aromatic hydrocarbons, such as chlorobenzene, o-dichlorobenzene, and 1,2,4-trichlorobenzene; (c) esters, such as ethyl acetate, butyl acetate, and ethyl butyrate; (d) ethers, such as ethyl ether, butyl ether, hexyl ether, octyl ether, anisole, ethoxybenzene, tetrahydrofuran, and dioxane; (e) hydrocarbons, such as pentane, hexane, heptane, octane, cyclohexane, benzene, toluene, and xylene; and any other organic solvents which satisfy the above-described requirement for water-solubility.

Particularly preferred specific organic solvents are dichloromethane, chlorobenzene, o-dichlorobenzene, and the like.

Although one of these specific organic solvents can be used independently, in order to suitably adjust the important characteristics such as the water-solubility, the amino acid-NCA solubility, and the like, it is desirable to use a mixture of two or more of the specific organic solvents.

There are no specific limitations on the water used in the preparation of the base emulsion.

Although there are no specific restrictions on the polymerization initiator used in the present invention so long as it is capable of inducing the polymerization reaction of the amino acid-NCA, it is desirable that such a polymerization initiator be dissolved in the specific organic solvent which is used. Amine compounds, metallic alcoholates, and the like are particularly preferred.

The following examples are given as the amine compound which can be used as the polymerization initiator: (a) primary amines, such as methylamine, ethylamine, isopropylamine, and butylamine; (b) secondary amines, such as dimethylamine, diethylamine, and dibutylamine; (c) tertiary amines, such as trimethylamine, triethylamine, and tributylamine; (d) alcohol amines, such as ethanolamine, diethanolamine, triethanolamine, and N,N-dimethylethanolamine; (e) polyamines, such as ethylenediamine, hexamethylenediamine N,N-dimethyl-1, 3-propanediamine, and triethylenediamine; and the like.

Specific examples of the metallic alcoholate include compounds consisting of an alcohol, such as methyl alcohol, ethyl alcohol, propyl alcohol, butyl alcohol, hexyl alcohol, 2-ethylhexyl alcohol, or benzyl alcohol, and a metallic element, such as lithium, sodium, or potassium.

These polymerization initiators can be used either individually or in combination of two or more.

Any emulsifiers which do not interfere with the polymerization reaction of the amino acid-NCA used and can homogeneously emulsify water and the specific organic solvent can be used as the emulsifier without any specific limitations. Nonionic emulsifiers are particularly preferred.

Specific examples of the nonionic emulsifier include polyoxyethylene alkyl ethers, polyoxyethylene alkylphenyl ethers, polyoxyethylene polyoxypropylene alkyl ethers, polyoxyethylene fatty acid esters, sorbitane fatty acid esters, polyoxyethylene sorbitane fatty acid esters, and glycerine fatty acid esters.

These emulsifiers can be used either individually or in combination of two or more.

The ratio by weight of water and the specific organic solvent used in process (1) is preferably 90:10 to 50:50, and particularly preferably 80:20 to 55:45. If the amount of the specific organic solvent is too small, the polymerization of amino acid-NCA tends to be depressed; if too large, it is occasionally difficult to produce a stable oil-in-water type base emulsion.

The amount of the emulsifier used varies depending on the identity of the amino acid-NCA, the specific organic solvent, and the emulsifier. A generally preferable amount is 0.01 to 3 parts by weight, particularly 0.03 to 1 parts by weight, per 100 parts by weight of the total amount of water and the specific organic solvent.

The amount of the amino acid NCA used per 100 parts by weight of the specific organic solvent is, for example, 1–100 parts by weight, and preferably 5–90 parts by weight. Because the amino acid-NCA can be polymerized even if incompletely dissolved in the specific organic solvent, it is not necessary to completely dissolve the amino acid-NCA in the specific organic solvent. Therefore, the maximum amount of the amino acid-NCA is not necessarily strictly limited by the maximum amount of the specific organic solvent.

The amount of the polymerization initiator used is, for example, 1/10 to 1/5000 mol, preferably 1/30 to 1/1000 mol, per 1 mol of the amino acid-NCA used.

In process (1), first, a medium for the polymerization reaction is produced by emulsifying the water and the specific organic solvent using the emulsifier. An ideal method is to add the amino acid-NCA to the base oil-in-water type emulsion thus-prepared and to polymerize the amino acid-NCA within droplets of the specific organic solvent with the further addition of the polymerization initiator.

There are no limitations on the method for preparing the base emulsion from water and the specific organic solvent. A method of mechanically stirring the mixture in a reaction vessel, a method of using ultrasonic waves, and a combination of these two methods are given as examples.

The amino acid-NCA may be added to the base emulsion by simply adding the amino acid-NCA powder to the base emulsion, by separately providing a specific organic solvent which may be the same as or different from the specific organic solvent used for the preparation of the base emulsion, adding the amino acid-NCA to this separately provided specific organic solvent, and then adding the mixture to the base emulsion, or by any other appropriate method. The amino acid-NCA may be added all at one time or may be added in portions.

The polymerization initiator may be added by adding the polymerization initiator in advance to the specific organic solvent used for the preparation of the base emulsion, by separately providing a specific organic solvent which may be different from that used for the preparation of the base emulsion, adding the polymerization initiator to this separately provided specific organic solvent, optionally together with the amino acid-NCA, and then adding this mixture to the base emulsion, or by any other appropriate method.

The polymerization reaction of the amino acid-NCA is initiated by causing the amino acid-NCA to contact the polymerization initiator. Although the polymerization temperature will vary depending on the identity of the amino acid-NCAs, the specific organic solvents, and the polymerization initiators which are used, the polymerization is carried out normally at −5° to 100° C., and preferably at 0° to 90° C. The poly-α-amino acid with the target molecular weight can be obtained by selecting the polymerization temperature from this range. The polymerization pressure is not specifically limited.

It is necessary to stir the reaction system to be emulsified during the polymerization reaction. The stirring is preferably done by a mechanical means in the reaction vessel at a rotation, usually, of 20–3000 rpm.

The reaction time for polymerizing the amino acid-NCA varies depending on the identity of the monomer, the specific organic solvent, and the polymerization initiator, but is usually 3 to 10 hours. The polymerization conversion rate is normally 90% or more, preferably 95% or more.

After completion of the polymerization of the amino acid-NCA, the specific organic solvent is removed from the produced poly-α-amino acid particles, thereby obtaining the target poly-α-amino acid particles.

Various means such as distillation can be used for removing the specific organic solvent. In this instance, the emulsifier in an amount of 0.05–10% by weight may be optionally added to the reaction product emulsion to stabilize the poly-α-amino acid particle emulsion.

Because the amino acid-NCA monomer is polymerized in the base emulsion of an oil-in-water type which satisfies specific conditions in process (1) as described above, the emulsion polymerization can be performed reliably while effectively suppressing hydrolysis of the amino acid-NCA. As a result, high molecular weight poly-α-amino acid particles can be easily prepared directly from α-amino acid.

Process (2) will now be illustrated.

The same amino acid-NCAs, polymerization initiators, emulsifiers, and water as described in the discussion of process (1) can be used in process (2).

In process (2), the polymerization initiator and the emulsifier are first added to water, and then the powder of amino acid-NCA is added.

The amino acid-NCA may be added all at one time, continuously, or in portions. The temperature of the water when the amino acid-NCA is added is usually −5° to 100° C., and preferably 0° to 90° C. There are no specific limitations on the polymerization pressure. It is desirable to add the amino acid-NCA while stirring the water.

The ratio by weight of the amino acid-NCA and water is usually 1:0.5 to 1:100, and preferably 1.1 to 1:50.

The ratio by weight of the emulsifier and the amino acid-NCA is usually 1:0.01 to 1:3, and preferably 1:0.03 to 1:1. If the amount of the emulsifier is less than 0.01 parts by weight per 1 part by weight of the amino acid-NCA, the resulting poly-α-amino acid tends to have a low molecular weight.

The ratio by weight of the polymerization initiator and the amino acid-NCA is 1:2 to 1:5000, and preferably 1:5 to 1:1000.

In the same manner as in process (1), the reaction system of process (2) must be kept emulsified by stirring during the addition of the amino acid-NCA and the polymerization reaction. The same stirring means and the same rate of rotation as in process (1) are applicable to process (2). Poly-α-amino acid particles with a desired molecular weight can be obtained by suitably selecting the polymerization temperature, and the kind and amount of amino acid-NCA and polymerization initiator.

The polymerization time and conversion rate in process (2) are the same as in process (1).

Although either the above-mentioned process (1) or process (2) can be used for the manufacture of the poly-α-amino acid particles of the present invention, process (2) is more preferable because of the capability of producing absolutely organic solvent-free poly-α-amino acid particles.

The average particle size of the poly-α-amino acid particles obtained by the processes of the present invention is in the range of 0.01 to 100 μm, and preferably 0.05 to 50 μm, with the coefficient or variation (CV value) for the average particle size being 1–30%, preferably 1 to 20%.

The molecular weight of the poly-α-amino acid of the present invention is 5000 to 500,000.

The limiting viscosity number of the poly-α-amino acid is about 0.2 to 2.

It is possible to make hollow particles of poly-α-amino acid by adding a poor solvent (a solvent in which poly-α-amino acid is only slightly soluble) to the poly-α-amino acid particles after the polymerization by process (1), allowing the mixture to stand for several minutes to several hours, and simultaneously removing the poor solvent and the specific organic solvent.

The addition of the poor solvent to the emulsion of poly-α-amino acid particles causes the polymer particles which, together with the specific organic solvent, make up the oil droplets in the produced emulsion, to be solidified from the surface of those droplets. The treatment for removing the specific organic solvent in this state causes the solvent to be removed from inside the particles while suppressing contraction of the particles, thereby producing poly-α-amino acid particles of which the inside may be hollow.

The poor solvent should be mutually soluble with water and the specific organic solvent and should not dissolve the produced polymer. Specific examples include lower alcohols, such as methyl alcohol, ethyl alcohol, and isopropyl alcohol, and lower ketones, such as acetone and methyl ethyl ketone.

The amount of the poor solvent used for 100 parts by weight of the poly-α-amino acid particles is preferably 1–50 parts by weight, and particularly preferably 2–30 parts by weight.

If this amount is less than 1 part by weight, there may be occasions when the efficiency of producing the hollow poly-α-amino acid particles is low. If this amount is larger than 50 parts by weight, on the other hand, the poly-α-amino acid particles may agglomerate and may not form an emulsion.

As a means for removing the poor solvent or both the poor solvent and the specific organic solvent, the same means for removing the specific organic solvent in process (1) can be used. By stirring the system while removing the poor solvent or both the poor solvent and the specific organic solvent, the dispersion medium on the surface of each particle is replaced by the poor solvent, thereby achieving sufficient contact of the poor solvent and the surface of the particles. As a result, the poor solvent or both the poor solvent and the specific organic solvent are removed together with part of the water.

This stirring operation can be mechanical stirring or stirring using ultrasonic waves.

The hollow poly-α-amino acid particles can be also produced by adding the poor solvent and then evaporating all the water, the specific organic solvent, and the poor solvent by spray drying or the like.

Furthermore, the poly-α-amino acid particles can be used after derivitization by the following methods. For example, when the poly-α-amino acid particles are made from an amino acid-NCA such as the N-carboxy anhydride of an acidic ester (e.g. glutamate, aspartate) or the N-carboxy anhydride of a basic amino acid (e.g. N-carboxybenzyloxylysine or N-carbobenzyloxyornithine), or when the particles of poly-α-amino acid are made from a copolymer of these amino acid-NCAs and an N-carboxy anhydride of a neutral amino acid (hereinafter referred to as copolymer particles).

It is possible to make the surface of particles hydrophilic by hydrolyzing that surface to produce an amino-group or a carboxy group. The surface of the copolymer particles can also be made hydrophilic by reacting these copolymer particles with an amino alcohol, such as ethanolamine, propanolamine, or buthanolamine. In addition, it is possible to cross-link inside the polymer particles by reacting these copolymer particles with a diamine such as ethylenediamine, propylenediamine, hexamethylenediamine, or octamethylenediamine; a glycol such as ethylene glycol or propylene glycol; or a dicarboxylic acid such as malonic acid, succinic acid, or adipic acid.

The poly-α-amino acid particles obtained by the process of the present invention may be used either as the emulsion or after separating from the aqueous medium.

The means for separating the poly-α-amino acid particles obtained by the present invention from the aqueous medium includes evaporating all the aqueous medium by a spray dryer or the like, precipitating solid poly-α-amino acid particles using a centrifuge and drying the solid precipitate, concentrating the poly-α-amino acid particle emulsion by means of a water-separating membrane and drying the resulting concentrate, and the like.

When the amount of poly-α-amino acid particles is small, freeze-drying is preferably employed as the method for drying these particles.

In addition, it is possible to remove the emulsifier by washing the poly-α-amino acid particles with water or the like.

The poly-α-amino acid particles prepared by the present invention are useful as novel raw materials for coating on papers, resins, rubbers and fibers, for encapsulating cosmetics, drugs, agricultural chemicals and fertilizers, and as particles for diagnostic reagents, as well as a variety of other applications.

The hollow particles of poly-α-amino acid are useful for drug delivery applications by encapsulating drugs therein, utilizing the in vivo degradation characteristics of the poly-α-amino acid; as sustained release agricultural chemicals or fertilizers by encapsulating the agricultural chemicals or fertilizers therein, utilizing the delayed decomposition of such poly-α-amino acid particles in the earth; and as cosmetics by encapsulating cosmetic ingredients in these poly-α-amino acid particles, utilizing the water-retention characteristics of poly-α-amino acids.

Other features of the invention will become apparent in the course of the following description of the exemplary embodiments which are given for illustration of the invention and are not intended to be limiting thereof.

EXAMPLES

In the Examples below, "% by weight" is simply designated as "%"; the average particle size of the polymer particles was measured by observing these polymer particles by transmission type electron microscopy; the CV number of polymer particles was calculated according to the formula, $$CV \text{ Number } (\%) = \left( \frac{\text{Standard deviation of the average particle size}}{\text{The average particle size}} \right) \times 100;$$

The limiting viscosity of polymers was measured in dichloroacetic acid at 30° C.; and the molecular weight of the polymer was calculated according to the formula, $$[\eta] = 2.78 \times 10^{-5} \times M^{0.87}$$

wherein $[\eta]$ is limiting viscosity and M is the molecular weight, in daltons.

Example 1

An oil-in-water type base emulsion was prepared by thoroughly emulsifying 50 g of water and 12.6 g of 1,2-dichloroethane (water solubility=0.9 g/100 ml at 1 atm, 25° C.) with 1 g of polyoxyethylene sorbitane monolaurate (Tween 20, trademark, manufactured by Kao Corp.). A solution was separately prepared by dissolving 1 g (3.8 mmol) of benzyl-L-glutamate-N-carbonic acid anhydride (hereinafter referred to as BLG-NCA) and 0.1 mmol of triethylamine in 12.6 g of 1,2-dichloroethane. This solution was added to the base emulsion, and the mixture was vigorously stirred. The BLG-NCA was polymerized at room temperature for 5 hours while stirring to maintain the emulsion, thus obtaining an emulsion of poly(benzyl-L-glutamate) particles. Poly(benzyl-L-glutamate) particles of the present invention were obtained by evaporating the specific organic solvent under vacuum.

The average particle size and the CV number of the poly(benzyl-L-glutamate) particles thus-obtained were 0.2 μm and 8%, respectively.

The poly(benzyl-L-glutamate) was coagulated by pouring the emulsion into methyl alcohol. The coagulated poly(benzyl-L-glutamate) was then dried, to obtain poly(benzyl-L-glutamate) particles at an yield of 91%. The resulting poly(benzyl-L-glutamate) had a limiting viscosity of 0.82 and a molecular weight of 137,000.

Examples 2–9

Poly-α-amino acid particles were prepared in the same manner as in Example 1, except for using the amino acid-NCAs, the specific organic solvents, the emulsifiers, and the polymerization initiators shown in Table 1 in the amounts indicated in Table 1, provided that in Example 4, triethylamine was added in advance to the base emulsion.

The average particle size and CV number of the resulting poly-α-amino acid particles, the yield, limiting viscosity, and molecular weight were measured. The results are shown in Table 1.

TABLE 1

| Example | α-Amino acid (g) | Specific organic solvent | Emulsifier | Polymerization initiator |
|---|---|---|---|---|
| 1 | BLG-NCA (1) | 1,2-Dichloroethane | Polyoxyethylene sorbitane monolaurate | Triethylamine |
| 2 | BLG-NCA (1) | Chlorobenzene | Polyoxyethylene sorbitane monolaurate | Triethylamine |
| 3 | BLG-NCA (1) | o-Dichlorobenzene | Polyoxyethylene sorbitane monolaurate | Triethylamine |
| 4 | BLG-NCA (1) | Chlorobenzene | Polyoxyethylene sorbitane monolaurate | Triethylamine |
| 5 | BLG-NCA (1) | 1,2-Dichloroethane | SDBS* | Triethylamine |
| 6 | BLG-NCA (1) | 1,2-Dichloroethane | Polyoxyethylene sorbitane monolaurate | Sodium ethylate |
| 7 | Methyl-L-glutamate-NCA | 1,2-Dichloroethane | Polyoxyethylene sorbitane | Triethylamine |

TABLE 1-continued

| | (1) | | monolaurate | |
|---|---|---|---|---|
| 8 | N-carbobenzoxy-L-lysine-NCA | 1,2-Dichloro-ethane | Polyoxyethylene sorbitane monolaurate | Triethylamine |
| 9 | (1) BLG-NCA/L-alanine-NCA (0.5/0.5) | 1,2-Dichloro-ethane | Polyoxyethylene sorbitane monolaurate | Triethylamine |

| Example | Type of polymer particles | Measurement conditions of CV number | Average particle size (μm) | CV Number of polymer particles (%) | Yield of polymer (%) | Limiting viscosity of polymer | Molecular weight of polymer |
|---|---|---|---|---|---|---|---|
| 1 | Filled | Emulsion | 0.2 | 8 | 91 | 0.82 | 137,000 |
| 2 | Filled | Emulsion | 0.2 | 8 | 87 | 0.87 | 147,000 |
| 3 | Filled | Emulsion | 0.3 | 9 | 87 | 0.79 | 131,000 |
| 4 | Filled | Emulsion | 0.7 | 10 | 77 | 0.58 | 92,000 |
| 5 | Filled | Emulsion | 0.3 | 9 | 72 | 0.44 | 67,000 |
| 6 | Filled | Emulsion | 0.2 | 12 | 99 | 0.88 | 149,000 |
| 7 | Filled | Emulsion | 0.2 | 15 | 84 | 0.31 | 45,000 |
| 8 | Filled | Emulsion | 0.3 | 9 | 91 | 0.83 | 139,000 |
| 9 | Filled | Emulsion | 0.5 | 10 | 80 | 0.43 | 65,000 |

*SDBS = Sodium dodecylbenzenesulfonate

Example 10

1 ml of methyl alcohol was gradually added to 30 g of the emulsion of poly(benzyl-L-glutamate) particles (solid component, 3%) obtained in Example 1, while stirring. The specific organic solvent was removed by vacuum distillation to obtain an emulsion of hollow particles of poly(benzyl-L-glutamate). The average particle size and CV number of the hollow particles were measured. The results are shown in Table 2.

30 ml of water was added to the emulsion of the hollow poly(benzyl-L-glutamate) particles. The mixture was stirred, centrifuged, and decanted. The steps of centrifugation and decantation were repeated twice to remove the emulsifier.

1 ml of water was added to the resulting solid. The mixture was stirred and freeze-dried to obtain a fine powder of hollow poly(benzyl-L-glutamate) particles. The polymer particles obtained were observed by transmission type electron microscopy to confirm that the inside was hollow.

Examples 11–16

Emulsions and powders of hollow poly-α-amino acid particles were prepared in the same manner as in Example 10, using the emulsions of poly-α-amino acid particles shown in Table 2 instead of the emulsion of hollow poly(benzyl-L-glutamate) emulsion particles prepared in Example 1. In the preparation of the poly(benzyl-L-glutamate) emulsion used in Example 12, polyoxyethylene polyoxypropylene alkyl ether was used as the emulsifier instead of polyoxyethylene sorbitane monolaurate of Example 1.

TABLE 2

| Example | Poly-α-amino acid particle emulsion | Type of polymer particles | Measurement conditions of CV number | Average particle size (μm) | CV Number of polymer particles (%) | Yield of polymer (%) | Limiting viscosity of polymer | Molecular weight of polymer |
|---|---|---|---|---|---|---|---|---|
| 10 | Emulsion obtained in Example 1 | Hollow | Emulsion | 0.2 | 8 | 91 | 0.82 | 137,000 |
| | | Hollow | Powder | 0.3 | 10 | | | |
| 11 | Emulsion obtained in Example 2 | Hollow | Emulsion | 0.2 | 8 | 87 | 0.87 | 147,000 |
| | | Hollow | Powder | 0.3 | 15 | | | |
| 12 | Emulsion obtained in Example 1 | Hollow | Emulsion | 0.2 | 7 | 72 | 0.84 | 135,000 |
| | | Hollow | Powder | 0.3 | 14 | | | |
| 13 | Emulsion obtained in Example 1 (30 g) SDBS*(0.5 g) | Hollow | Emulsion | 0.2 | 7 | 91 | 0.82 | 137,000 |
| | | Hollow | Powder | 0.3 | 12 | | | |
| 14 | Emulsion obtained Example 7 | Hollow | Emulsion | 0.2 | 9 | 84 | 0.31 | 45,000 |
| | | Hollow | Powder | 0.3 | 14 | | | |
| 15 | Emulsion obtained in Example 8 | Hollow | Emulsion | 0.3 | 8 | | | |
| | | Hollow | Powder | 0.3 | 14 | | | |
| 16 | Emulsion obtained in Example 9 | Hollow | Emulsion | 0.5 | 9 | 80 | 0.43 | 65,000 |
| | | Hollow | Powder | 0.3 | 14 | | | |

*SDBS: Sodium dodecylbenzenesulfonate

Example 17

0.2 g of Tween 20 and 0.072 mmol of triethylamine were added to 20 ml of water. The mixture was stirred, followed by the addition of 0.5 g (1.9 mmol) of BLG-NCA powder. BLG-NCA was polymerized at room temperature for 5 hours while stirring to obtain an emulsion of poly(benzyl-L-glutamate) particles.

The average particle size and the CV number of the poly(benzyl-L-glutamate) particles were 12 μm and 19%, respectively.

The poly(benzyl-L-glutamate) was coagulated by pouring this emulsion into methyl alcohol. The coagulated poly(benzyl-L-glutamate) was then dried to obtain poly(benzyl-L-glutamate) at a yield of 92%. The poly(benzyl-L-glutamate) had a limiting viscosity of 0.35 and a molecular weight of 51,000.

Examples 18–22

Poly-α-amino acid particles were prepared in the same manner as in Example 17 using the amino acid-NCAs, the emulsifiers, and the polymerization initiators shown in Table 3 in the amounts indicated in Table 3.

The average particle size and CV number of the resulting poly-α-amino acid particles, the yield, limiting viscosity, and molecular weight were measured. The results are shown in Table 3.

Comparative Example 2

The same experiment as in Example 1 was carried out, except for using tetrahydrofuran instead of 1,2-dichloroethane. Because tetrahydrofuran is miscible with water in all proportions, the resulting mixture was a homogeneous solution in tetrahydrofuran and water, not an emulsion.

The solution obtained after the polymerization was poured into 300 ml of methyl alcohol to coagulate the poly(benzyl-L-glutamate), and the coagulate was dried. The yield, limiting viscosity, and molecular weight of the resulting fine powder of poly(benzyl-L-glutamate) were measured. The results are shown in Table 4.

Comparative Example 3

A solution of poly(benzyl-L-glutamate) was prepared by adding 1.0 g of BLG-NCA and 0.7 mmol of triethylamine to 60 ml of dichloromethane, and subjecting the mixture to solution polymerization at room temperature for 20 hours.

TABLE 3

| Example | α-Amino acid (g) | Emulsifier | Polymerization initiator | Type of polymer particles | Measurement conditions of CV number | Average particle size (μm) | CV Number of polymer particles (%) | Yield of polymer (%) | Limiting viscosity of polymer | Molecular weight of polymer |
|---|---|---|---|---|---|---|---|---|---|---|
| 17 | BLG-NCA (0.5) | Polyoxyethylene sorbitane monolaurate | Triethylamine | Filled | Emulsion | 12 | 19 | 92 | 0.35 | 51,000 |
| 18 | BLG-NCA (0.5) | Polyoxyethylene sorbitane monolaurate | Triethylamine (0.2 ml) | Filled | Emulsion | 10 | 17 | 90 | 0.22 | 3 1,000 |
| 19 | BLG-NCA (0.5) | Polyoxyethylene lauryl ether | Triethylamine | Filled | Emulsion | 1 1 | 20 | 93 | 0.43 | 65,000 |
| 20 | BLG-NCA (0.5) | Polyoxyethylene sorbitane monolaurate | Trietnylamine | Filled | Emulsion | 12 | 23 | 92 | 0.44 | 67,000 |
| 21 | γ-Ethyl-L-glutamate-NCA (0.5) | Polyoxyethylene sorbitane monolaurate | Triethylamine | Filled | Emulsion | 9 | 17 | 74 | 0.46 | 21,000 |
| 22 | N-carbobenzoxy-L-lysine-NCA (0.5) | Polyoxyethylene sorbitane monolaurate | Triethylamine | Filled | Emulsion | 14 | 25 | 96 | 0.38 | — |

Comparative Example 1

A solution of poly(benzyl-L-glutamate) was prepared by adding 1.0 g of BLG-NCA and 0.1 mmol of triethylamine to 60 ml of dichloromethane, and subjecting the mixture to solution polymerization at room temperature for 20 hours.

This solution of poly(benzyl-L-glutamate) was divided into two equal portions. To one of the portions were added 50 ml of water and 0.5 g of polyoxyethylene sorbitane monolaurate, followed by sufficient stirring to emulsify the mixture. The specific organic solvent was removed by vacuum distillation, and the residue was again emulsified. The average particle size and the CV number of the polymer particles in the resulting emulsion are shown in Table 4.

The other portion of the polymer solution was poured into 300 ml of methyl alcohol to coagulate poly(benzyl-L-glutamate), and the coagulate was dried. The yield, limiting viscosity, and molecular weight of the poly(benzyl-L-glutamate) were measured. The results are shown in Table 4.

This polymer solution was divided into two equal portions. One of the portions and 50 ml of water were thoroughly emulsified with the addition of 0.5 g of oxyethylene sorbitane monolaurate, to obtain an oil-in-water type emulsion. 1 ml of methyl alcohol was gradually added to the emulsion while stirring, and the specific organic solvent was removed by vacuum distillation. The residue was again emulsified. On the other hand, the other portion of the polymer solution was poured into 300 ml of methyl alcohol to coagulate the produced poly(benzyl-L-glutamate), and the coagulate was dried.

The average particle size and the CV number of the polymer particles in the emulsion obtained above, and the yield, limiting viscosity, and molecular weight of the poly(benzyl-L-glutamate) were measured. The results are shown in Table 4.

The polymer particles in the above emulsion were observed by transmission-type electron microscopy to confirm that these polymers were not hollow.

TABLE 4

| Comparative Example | Type of polymer particle | Measurement conditions of CV number | Average particle size (μm) | CV Number of polymer particles (%) | Yield of polymer (%) | Limiting viscosity of polymer | Molecular weight of polymer |
|---|---|---|---|---|---|---|---|
| 1 | Filled | Emulsion | 2.8 | 65 | 78 | 0.83 | 139,000 |
| 2 | Filled | — | — | — | 5 | 0.06 | 3,800 |
| 3 | Filled | Emulsion | 1.8 | 65 | 91 | 0.83 | 139,000 |

An oil-in-water type base emulsion which satisfies specific conditions is used as the medium for the polymerization in the present process. The amino acid-NCA monomer is either polymerized by being added to this emulsion or polymerized in water as being coated with an emulsifier. This ensures that the amino acid-NCA will be reliably polymerized by the emulsion polymerization, while effectively suppressing hydrolysis of the amino acid-NCA. As a result, poly-α-amino acid particles with a large molecular weight can be easily produced directly from the monomer.

Because the particle size of poly-α-amino acid particles obtained is dependent upon the particle size conditions of oil droplets of the specific organic solvent in the base emulsion, it is possible to reliably and easily prepare an emulsion of poly-α-amino acid particles with a small average particle size and a narrow particle size distribution by appropriately controlling the particle size conditions of the oil droplets in the emulsion.

In addition, hollow polymer particles, each particle having a vacant space therein, can be prepared by adding a poor solvent to the emulsion of poly-α-amino acid particles obtained using the specific organic solvent of the present invention. It is therefore possible to produce poly-α-amino acid particles having a desired average particle size and a vacant hollow space in each particle.

As mentioned above, emulsions of poly-α-amino acid particles having a desired average particle size, dispersed in an aqueous medium, can be easily manufactured on an industrial scale.

This application is based on Japanese patent applications 240751/1991, filed on Sep. 9, 1994, and 287198/1994, filed on Oct. 28, 1994, which are incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A process for preparing poly-α-amino acid particles which comprises:
   (a) preparing an oil-in-water emulsion comprising water, an organic solvent having a water solubility of 10 g/100 ml or less at 1 atm at 25° C., and an emulsifier;
   (b) polymerizing an α-amino acid-N-carboxy anhydride by emulsion polymerization in said oil-in-water emulsion; and
   (c) removing said organic solvent;
   wherein said organic solvent is selected from the group consisting of halogenated aliphatic hydrocarbons, halogenated aromatic hydrocarbons, esters, ethers and hydrocarbons.

2. The process according to claim 1, wherein said organic solvent is capable of dissolving at least 0.1 g of said α-amino acid-N-carboxy anhydride in 100 ml.

3. The process according to claim 1, wherein said α-amino acid-N-carboxy anhydride is present in said oil-in-water emulsion in an oil phase.

4. The process according to claim 1, wherein a solid α-amino acid-N-carboxy anhydride is added to said oil-in-water emulsion and polymerized.

5. The process according to claim 1, wherein said α-amino acid-N-carboxy anhydride is selected from the group consisting of γ-methyl glutamate-N-carboxy anhydride, γ-ethyl glutamate-N-carboxy anhydride, γ-benzyl glutamate-N-carboxy anhydride, and carbobenzoxy-L-lysine-N-carboxy anhydride.

6. A process for preparing poly-α-amino acid particles, comprising:
   polymerizing an α-amino acid-N-carboxy anhydride in an aqueous medium comprising water, an emulsifier, and a polymerization initiator.

7. The process according to claim 6, wherein said polymerization includes preparing a mixture of water, a polymerization initiator, and an emulsifier and adding a solid α-amino acid N-carboxy anhydride into said mixture.

8. The process according to claim 6, wherein said α-amino acid-N-carboxy anhydride is selected from the group consisting of γ-methyl glutamate-N-carboxy anhydride, γ-ethyl glutamate-N-carboxy anhydride, γ-benzyl glutamate-N-carboxy anhydride, and carbobenzoxy-L-lysine-N-carboxy anhydride.

9. A process for preparing hollow poly-α-amino acid particles which comprises:
   (a) preparing an oil-in-water emulsion from water, an organic solvent having a water solubility of 10 g/100 ml or less at 1 atm at 25° C., and an emulsifier;
   (b) polymerizing an α-amino acid N-carboxy anhydride by emulsion polymerization in said oil-in-water emulsion to produce poly-α-amino acid polymer particles;
   (c) adding a solvent in which the poly-α-amino acid is only slightly soluble to the poly-α-amino acid polymer particles; and
   (d) removing said solvents;
   wherein said organic solvent is selected from the group consisting of halogenated aliphatic hydrocarbons, halogenated aromatic hydrocarbons, esters, ethers and hydrocarbons; and
   said solvent in which the poly-α-amino acid is only slightly soluble is selected from the group consisting of methyl alcohol, ethyl alcohol, isopropyl alcohol, acetone and methyl ethyl ketone.

10. Poly-α-amino acid particles, having:
(a) an average particle size of 0.01 to 100 μm;
(b) a coefficient of variation for the average particle size of 1 to 30%; and
(c) a molecular weight of the poly-α-amino acid of 5,000 to 500,000 daltons,
wherein each of said particles comprises a hollow space.

11. The poly-α-amino acid particles of claim 10, wherein said average particle size is 0.05 to 50 μm.

12. The process according to claim 1, wherein said organic solvent is selected from the group consisting of chloromethane, dichloromethane, chloroform, 1,1-dichloroethane, 1,2-dichloroethane, 1,1,2-trichloroethane, chlorobenzene, o-dichlorobenzene, 1,2,4-trichlorobenzene, ethyl acetate, butyl acetate, ethyl butyrate, ethyl ether, butyl ether, hexyl ether, octyl ether, anisole, ethoxybenzene, pentane, hexane, heptane, octane, cyclohexane, benzene, toluene, xylene and mixtures thereof.

13. The process according to claim 9, wherein said organic solvent is selected from the group consisting of: chloromethane, dichloromethane, chloroform, 1,1-dichloroethane, 1,2-dichloroethane, 1,1,2-trichloroethane, chlorobenzene, o-dichlorobenzene, 1,2,4-trichlorobenzene, ethyl acetate, butyl acetate, ethyl butyrate, ethyl ether, butyl ether, hexyl ether, octyl ether, anisole, ethoxybenzene, pentane, hexane, heptane, octane, cyclohexane, benzene, toluene, xylene and mixtures thereof.

14. The process according to claim 1, wherein said organic solvent is selected from the group consisting of dichloromethane, chlorobenzene, o-dichlorobenze and mixtures thereof.

15. The process according to claim 9, wherein said organic solvent is selected from the group consisting of dichloromethane, chlorobenzene, o-dichlorobenze and mixtures thereof.

* * * * *